United States Patent
Mushahwar et al.

(10) Patent No.: US 10,888,698 B2
(45) Date of Patent: Jan. 12, 2021

(54) APPARATUS AND METHOD FOR PREVENTION AND MITIGATION OF DEEP VEIN THROMBOSIS

(71) Applicant: BIOTECHNOLOGY & HEALTH INNOVATIONS INC., Edmonton (CA)

(72) Inventors: Vivian K. Mushahwar, Edmonton (CA); Einat Ravid, Edmonton (CA); David Shaun Gray, Edmonton (CA)

(73) Assignee: BIOTECHNOLOGY & HEALTH INNOVATIONS INC., Edmonton (CA)

( * ) Notice: Subject to any disclaimer, the term of this patent is extended or adjusted under 35 U.S.C. 154(b) by 0 days.

(21) Appl. No.: 14/856,200

(22) Filed: Sep. 16, 2015

(65) Prior Publication Data
US 2016/0074654 A1    Mar. 17, 2016

Related U.S. Application Data

(60) Provisional application No. 62/051,186, filed on Sep. 16, 2014.

(51) Int. Cl.
*A61N 1/36* (2006.01)
*A61N 1/04* (2006.01)

(52) U.S. Cl.
CPC ....... *A61N 1/36003* (2013.01); *A61N 1/0452* (2013.01); *A61N 1/0484* (2013.01); *A61N 1/36034* (2017.08)

(58) Field of Classification Search
CPC . A61N 1/0452; A61N 1/0484; A61N 1/36014
See application file for complete search history.

(56) References Cited

U.S. PATENT DOCUMENTS

| | | | | |
|---|---|---|---|---|
| 5,556,422 A | * | 9/1996 | Powell, III | A61N 1/36014 607/48 |
| 5,782,893 A | | 7/1998 | George | |
| 6,002,965 A | * | 12/1999 | Katz | A61N 1/321 128/DIG. 15 |
| 6,214,032 B1 | * | 4/2001 | Loeb | A61N 1/08 607/1 |
| 6,226,552 B1 | * | 5/2001 | Staunton | A61N 1/36014 607/72 |
| 7,308,303 B2 | * | 12/2007 | Whitehurst | A61M 5/14276 607/3 |

(Continued)

FOREIGN PATENT DOCUMENTS

| | | |
|---|---|---|
| WO | 2011087539 | 7/2011 |
| WO | 2013069002 | 5/2013 |

*Primary Examiner* — Michael J D Abreu
(74) *Attorney, Agent, or Firm* — Holzer Patel Drennan

(57) ABSTRACT

Apparatus and methodologies for the mitigation and prevention of venous thromboembolism-related disorders resulting from by venous blood stasis. More specifically, repeated cycles of brief bouts of intermittent electrical stimulation are repeated every several minutes to contract at least one target muscle, causing a temporary increase in venous blood flow and blood velocity in the veins in the region of the target muscle(s). The present intermittent electrical stimulation paradigm may be used to mimic physiological responses following voluntary contraction of the target muscle(s), without fatiguing the muscle(s).

17 Claims, 7 Drawing Sheets

(56) References Cited

U.S. PATENT DOCUMENTS

| | | |
|---|---|---|
| 8,874,223 B2 | 10/2014 | Mushahwar |
| 2005/0251067 A1* | 11/2005 | Terry ................... A61H 1/0266 601/5 |
| 2006/0085047 A1* | 4/2006 | Unsworth .......... A61N 1/36014 607/48 |
| 2007/0049814 A1* | 3/2007 | Muccio ................ A61N 1/0452 600/388 |
| 2011/0071595 A1* | 3/2011 | Muccio ................ A61N 1/0452 607/48 |
| 2012/0041513 A1 | 2/2012 | Tudor |
| 2013/0085420 A1 | 4/2013 | Feinstein |
| 2015/0182746 A1* | 7/2015 | Tucker ................... A61N 1/321 602/2 |
| 2015/0245976 A1 | 9/2015 | Jackson et al. |

\* cited by examiner

APPARATUS AND METHOD FOR PREVENTION AND MITIGATION OF DEEP VEIN THROMBOSIS

RELATED APPLICATIONS

This application claims priority to U.S. Provisional Patent Application No. 62/051,186, filed Sep. 16, 2014, entitled "APPARATUS AND METHOD FOR PREVENTION AND MITIGATION OF DEEP VEIN THROMBOSIS," the entirety of which is incorporated herein by reference as if set forth in full.

TECHNICAL FIELD

Apparatus and methodologies for the mitigation and prevention of venous thromboembolism caused by venous blood stasis and, in particular, the mitigation and prevention of deep vein thrombosis is provided. More specifically, apparatus and methodologies for the mitigation and prevention of venous thromboembolism by electrical stimulation are provided.

BACKGROUND

Deep vein thrombosis (DVT) is a condition that can commonly lead to pulmonary embolism (PE) and certain death. Pulmonary emboli resulting from thrombi originally developed in deep veins of the legs constitute at least 90% of the cases. Collectively, DVT and PE are referred to as venous thromboembolism (VTE), which commonly occurs when the individual is hospitalized, and impacts nearly 1 million people in the United States each year. With approximately 300,000 people dying from PE, it has become the most common avoidable condition causing hospital-related death. Further, once a DVT occurs, more than 50% of patients develop post-thrombotic syndrome (PTS). Symptoms associated with PTS include chronic leg pain, swelling or redness of the legs, and ulcers. PTS is difficult to treat, further reduces mobility and the associated pain and discomfort further reduce quality of life. The primary remedy for VTE and PTS is to mitigate or prevent the formation of DVT altogether.

Prevention of DVT, which almost always leads to PE, is a primary directive for hospital patients in the US, Canada and other developed countries. For example, the Agency for Healthcare Research and Quality (AHRQ) in the US has identified thrombosis prevention as the top priority among approximately 80 evidence-based practices with the greatest potential to improve the safety of hospitalized patients. A call to action by the US Surgeon General further exemplifies the urgency for finding effective means for preventing DVT. In Alberta, Canada, a newly established VTE initiative has become heavily focused on evidence-based means for preventing DVT and subsequent PE. In general, the risk of VTE in hospitalized patients is 100-fold higher than that for people living in the community. In the US, about 4,000,000 surgical patients and 8,000,000 medical patients are at moderate to high risk for VTE each year.

Where blood is static, DVT occurs rapidly (e.g., ~2-7 minutes). For this reason, DVT is particularly prevalent in people with reduced mobility, including patients undergoing or recovering from major surgical procedures or orthopedic surgery, patients in coma, patients with major trauma, patients with paralysis or paresis of the lower extremities, or patients with a plaster cast. Additional DVT risk factors include cancer, use of oral contraceptives or hormonal replacement therapy, antiphospholipid syndrome, myeloproliferative disorders, polycythemia vera, receiving central venous catheters, age, obesity or defective venous valves. DVT also commonly affects women during pregnancy and post-partum.

A primary challenge with DVT is the difficulty of diagnosing it. Therefore, prophylactic measures are commonly used. The most common prophylactic treatment for DVT in hospitalized patients is the use of blood thinners (anticoagulants) such as heparin, however such a treatment is not always effective and cannot be used in patients with bleeding disorders. Further, blood thinners are often combined with other known treatments to provide better outcomes than those achieved by one intervention alone.

Compression socks, usually worn on the lower legs, apply constant pressure with the aim of reducing the extent of blood pooling. While compression socks have long been prescribed as a means for preventing DVT, their effectiveness in doing so has not been demonstrated.

Another commonly used prophylaxis is intermittent pneumatic compression (IPC), comprising a mechanical system that sequentially inflates and deflates pads placed around the person's limbs to mobilize the blood, increasing its flow back towards the heart. Such pads are designed to occlude the patient's vessels by compressing the veins, then opening them by releasing the compressive pressure, leading to a burst of blood flow through the veins. For example, United States Patent Application No. US2015/0245976 teaches an improved garment or cuff for the prophylaxis treatment of DVT. The garment is inflatable, comprising a plurality of chambers arranged adjacent to one another along the length of the garment enabling a particular pressure profile to be provided across the garment, and thus the person's limb.

Despite the current push to globalize the use of IPC, such systems have several faults that hamper their wide-spread application. For example, IPC pads can be difficult for health care providers to position in place and remove, and are uncomfortable for the patient. The pads and associated pumps are large and heavy, further reducing the patient's ability to move and the health care provider's ability to turn patients in bed. Removing the system and repositioning it to allow for toileting activities is cumbersome and time consuming Misdirected vein compression from pad misplacement or misuse can actually induce thrombosis. The IPC pumps are loud, disrupting the patient's ability to sleep, and skin chaffing by the pads is a common side-effect of the system. Moreover, once discharged from the hospital, patients cannot take the IPC system with them despite still being at high risk of developing DVTs. Collectively, these factors have led to a high rejection rate of IPCs by patients. Such systems also fail to mitigate other known symptoms associated with reduced mobility, such as muscle spasticity and subsequent contractures.

In an attempt to overcome the problems with IPC devices, electrical stimulation techniques for stimulating the person's muscles have also been used to prevent DVT. All electrical stimulation devices are designed to mimic a heartbeat (e.g., stimulus frequency of ~50-120 pulses per minute), triggering repetitive muscle contractions to "pump" blood through the veins. Such treatments, however, have failed because the repetitive stimulation required to mobilize the blood rapidly fatigues the muscle and renders it incapable of continued contraction. Recovery from muscle fatigue takes several hours and, for this reason, known electrical stimulation treatments can only be administered for short periods of time (e.g., 15-30 minutes) between long relaxation periods (e.g., 6-8 hours). For example, United States Patent Application No. US 2003/0158583 teaches an electromagnetic stimulation device that may be used in the prevention of deep vein thrombosis, however the device can only be used for 20 minutes each day, in two 10-minute increments spaced 4-8 hours apart. Even where the treatment regime can include 15-minute treatments spaced 20 minutes apart, such frequency of use is ineffective for preventing DVT, which can readily develop in the period of no electrical stimulation. Further, other systems also require the stimulator or sticky electrodes to be positioned directly on the body, complicating the administration and efficacy of the device and causing uncomfortable hair entanglement issues.

Other known electrical stimulation devices attempt to enhance lower extremity blood flow by selectively stimulating localized lower limb muscles. For example, US Patent Application No. 2005/0251067 teaches a device that can stimulate contraction of the patient's foot to contract and elongate muscles of the lower leg. Such a system, however, requires that the patient be in a reclined position (e.g., in a bed, on a table, or in the leg support of a seat) while the patient's foot is flexed and extended. Other systems, such as the device taught in U.S. Pat. No. 5,782,893, teach the use of electrodes placed on the patient's calves, but such devices still teach the application of stimulation paradigms that mimic the heartbeat (e.g., symmetrical patterns of 5 seconds and 5 seconds off), which will rapidly fatigue the muscle and can only be used for short periods of time (e.g., a few hours at a time).

SUMMARY

The inventors have determined that a need exists for apparatus and methodologies for using electrical stimulation to mitigate or prevent DVT, particularly in the lower extremities, such system providing a small, reliable, easy-to-use, lightweight, mobile device that can be used continuously and effectively over long periods of time (e.g. ~24 hours a day) without discomfort or muscle fatigue. It is desirable that such a system may be quiet and innocuous.

Apparatus and methodologies are provided for the mitigation and prevention of venous thromboembolism-related disorders resulting from by venous blood stasis. More specifically, repeated cycles of brief bouts of intermittent electrical stimulation are repeated every several minutes to contract at least one target muscle in a person having compromised blood flow, causing a temporary increase in venous blood flow and blood velocity in the veins associated with the target muscle(s). The present intermittent electrical stimulation paradigm may be used to mimic physiological responses following voluntary contraction of the target muscle(s), without fatigue the muscle(s).

More specifically, a method of electrically stimulating at least one target muscle is provided for the mitigation or prevention of venous blood stasis in a person having compromised blood flow, wherein the method comprises repeating cycles of electrical stimulation provided for a predetermined period of time, contracting the at least one target muscle and increasing both venous blood flow and blood velocity in deep veins associated with the target muscle(s), and ceasing the electrical stimulation for a predetermined period of time, relaxing the at least one target muscle and returning venous blood flow and blood velocity in the deep veins associated with the target muscle(s) to pre-stimulation levels. The predetermined periods of electrical stimulation and cessation are selected to mimic mobilization of venous blood flow and venous blood velocity following voluntary (i.e., 'normal') fused muscle contractions of the at least one target muscle. In other words—the predetermined periods of electrical stimulation and cessation may be selected to mimic physiological actions or responses to venous blood flow and blood velocity following voluntary muscle contractions in individuals that do not suffer from compromised blood flow.

In embodiments herein, the predetermined period of electrical stimulation is shorter than the predetermined period of electrical cessation. More specifically, the predetermined period of electrical stimulation may comprise a brief bout of stimulation lasting seconds, and repeated every several minutes. The predetermined period of stimulation may be in the range of 0.1 to 5 seconds, in the range of 1 to 3 seconds, or may be approximately 2 seconds. The predetermined period of electrical cessation may be in the range of 1 to 10 minutes, in the range of 1 to 5 minutes, or approximately 3 minutes. In one embodiment, the predetermined period of electrical stimulation may last 2 seconds and repeated every 3 minutes. The present intermittent electrical stimulation paradigm may be repeated for a period of up to 24 hours a day (or longer).

In some embodiments herein, the at least one target muscle may be selected in order to mitigate or prevent venous blood stasis in veins associated with the target muscle(s), or proximal to the muscle, wherein the deep veins are prone to venous thromboembolism.

In other embodiments herein, a device for electrically stimulating at least one target muscle is provided for the mitigation or prevention of venous blood stasis in a person having compromised blood flow, wherein the device comprises at least one electrode adapted to electrically stimulate the at least one target muscle, at least one stimulator, electrically coupled to the at least one electrodes, wherein the stimulator is programmed and operable to initiate the at least one electrode to electrically stimulate the at least one target muscle, increasing both venous blood flow and venous blood velocity in at least one deep vein associated with (e.g., in the region of) the target muscle, for a predetermined period of stimulation and to cease electrical stimulation for a predetermined period of cessation, returning venous blood flow and blood velocity in the deep veins to pre-stimulation levels.

More specifically, a device for intermittently electrically stimulating at least one target muscle for the mitigation or prevention of venous blood stasis in a person having compromised blood flow is provided, the device is operative to operative to generate a discrete signal, a continuous signal, or a combination thereof, at a frequency in the range of 20 Hz to 60 Hz, or approximately 40 Hz. The present device may be adapted to provide the stimulator and at least one electrode in a flexible garment.

DESCRIPTION OF THE EMBODIMENTS

Apparatus and methodologies for using intermittent electrical stimulation to mitigate or prevent venous blood stasis are provided, including the mitigation and prevention of venous thromboembolism and related disorders, such as deep vein thrombosis (DVT). More specifically, apparatus and methods are provided for electrically stimulating the muscles of an individual having compromised blood flow (e.g. venous blood flow) in a manner that simulates physiological responses (e.g., the mobilization of venous blood flow) that occur following voluntary 'normal' muscle contractions during common activities such as walking, standing, exercising or adjusting one's posture. Electrical stimulation of the muscle(s) according to embodiments herein can increase both venous blood velocity and blood flow with single stimulus pulses or brief trains of stimuli (e.g. in the order of seconds) every few minutes. Such stimulus pulses or brief trains of stimuli may be provided in a manner to mimic a form of muscle contraction (e.g. muscle deformation or reshaping) that occurs in mobile individuals, causing mobilization of blood in the veins, without using an external source to mechanically compress the muscle, without attempting to mimic the heartbeat, and without fatiguing the muscle.

Figure 1:
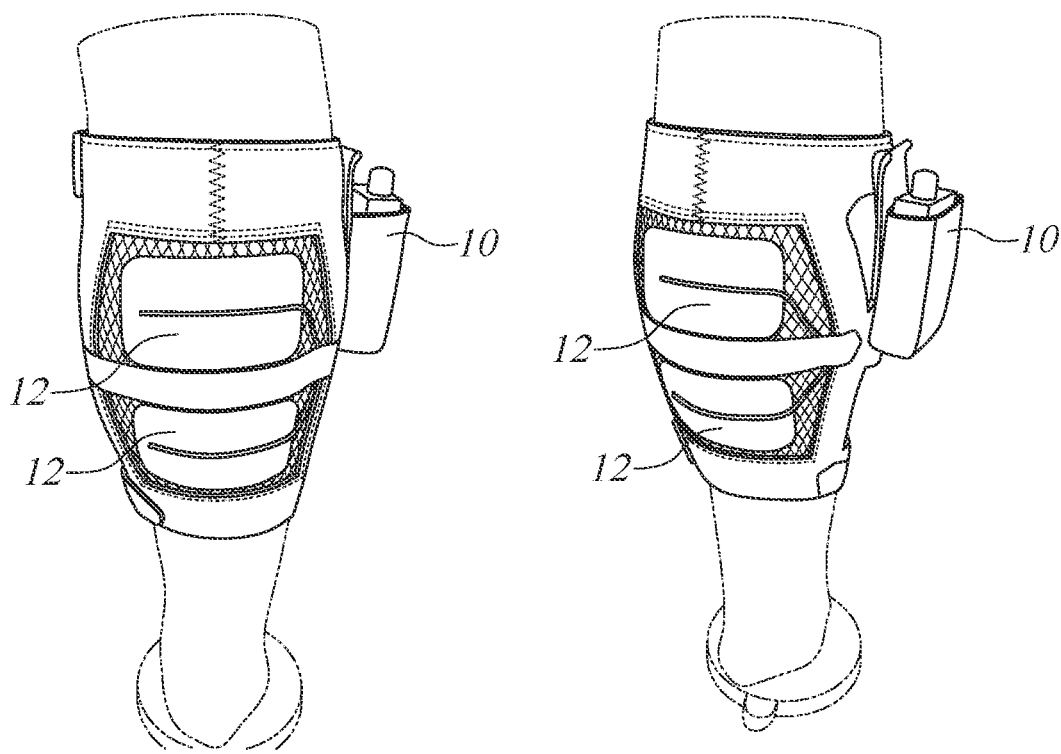
FIG. 1 shows the present apparatus positioned on a user's calf muscle according to embodiments herein.

Having regard to FIG. 1, the present system may comprise a stimulator 10 electrically coupled to at least one electrode 12, having an anode and a cathode, via respective electrical leads. The at least one electrode 12 may be positioned, directly or indirectly, on a person's skin at or near at least one target muscle, such that the electrical stimulus transmitted from the electrodes 12 to the muscles causes contraction of the muscle(s).

The stimulator 10 may be any appropriate device for generating an electrical signal such as a discrete signal (e.g., pulsatile waveform), a continuous signal (e.g., sustained sinusoidal waveform, rectangular waveform), or a combination of a discrete signal and a continuous signal. The electrical signal may be transmitted at a characteristic frequency of 20 Hz to 60 Hz, and preferably, the electrical signal is transmitted at a characteristic frequency of ~40 Hz. The stimulator may be battery operated. Electrode burns can be mitigated by measuring the impedance of the electrode-skin interface and by regulating the amount of voltage applied by the stimulator 10 across the interface.

The at least one electrodes 12 may be positioned on a muscle proximate the target area of the person, that is—proximate an area where the person has reduced or compromised blood circulation and is at the highest risk of thrombus formation (e.g., where blood is or may become static). Positioning of the at least one electrode 12 may vary depending upon the user and the target muscle, provided that the target muscle (e.g., upper or lower extremities) is one that undergoes contraction, compressing the deep veins associated with, or in the local region of, the muscle.

The at least one target muscle(s) may be selected in order to mitigate or prevent venous blood stasis whereby contraction of the muscle(s) at least partially compresses the venous wall, mobilizing venous blood, in deep veins proximally associated with the muscle(s), optimally where such veins may be prone to venous thromboembolism. For example, the at least one target muscle selected may be one or more calf muscle(s) that, when contracted, cause a change in venous blood flow and blood velocity in the deep veins within or near the calf muscle (e.g., the popliteal vein and/or the femoral vein, which may both be proximally associated or "in the region of" with the calf muscle).

Once the at least one electrode(s) 12 are in position, the stimulator 10 may be used to initiate the transmission of an electrical stimulus to the skin portion of the person according to embodiments herein. The at least one electrode 12 may be adapted to transmit an electrical stimulus sufficient to effect fused muscle contraction of the at least one target muscle(s) in a manner to cause a temporary increase in venous blood flow and venous blood velocity, thereby reducing the risk of thrombus formation. The electrical stimulus may be selected to mimic optimal strengths of fused muscles contractions on venous blood velocity and blood flow (e.g., such strengths varying between voluntary contractions of certain muscles such as, for example, flexor and extensor muscles, or co-contraction of both flexor and extensor muscles). In some embodiments, the electrical stimulus may be selected to achieve an increase in deep vein blood flow by up to approximately 20 fold (e.g., from baseline blood flow in the vein being compressed by the muscle contraction). It should be understood that the increase in venous blood flow and venous blood velocity may be the highest as the muscle contraction forms (e.g., soon after the start of the electrical stimulus), where compression of the muscle 'squeezes' the vein, compressing the venous wall and 'pushing' the blood back towards the heart.

More specifically, the stimulator 10 may be programmed and operable to transmit a predetermined pattern of electrical stimulation comprising: a) initiating the at least one electrode 12 to electrically stimulate the target muscle(s) for a brief predetermined bout or period of stimulation (the "ON" period), contracting the muscle(s) and causing an increase in venous blood flow and velocity, and b) ceasing the electrical stimulation to the target muscle(s) for a predetermined period of cessation (the "OFF" period), returning the venous blood flow and velocity back to pre-stimulation levels. Optimally, the present stimulator 10 may be adapted to provide the electrical stimulus in an asymmetric paradigm, that is—to provide long durations (minutes) of muscle relaxation in between brief bouts (seconds) of electrical stimulation.

Figure 2:
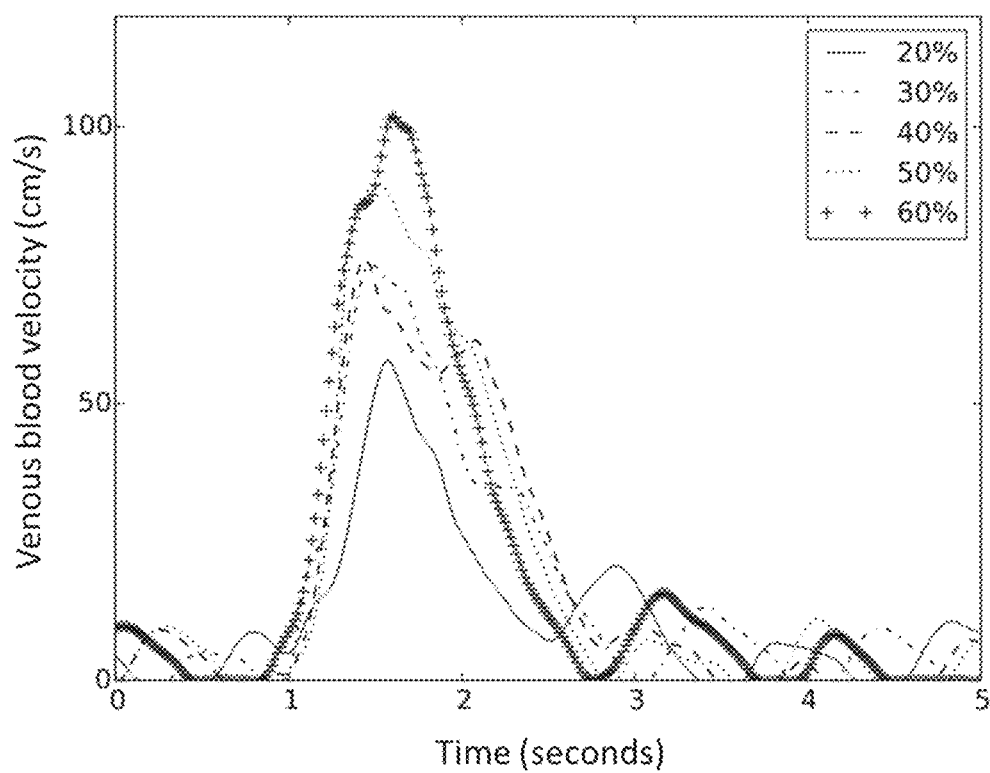
FIG. 2 shows changes in venous blood velocity produced by voluntary plantarflexion movements of the ankle at various levels of muscle contraction strengths.

Having regard to FIG. 2, the electrical stimulus initiated during the ON period may be sufficient to effect contraction of the target muscle(s), 'pushing' on the target veins associated with the muscle(s) (e.g., the popliteal, femoral, iliac veins, or other main veins of the legs where DVT occurs) and, at least partially, decreasing the diameter of the venous wall and temporarily increasing venous blood flow therein. It should be understood that electrically-stimulated dynamic contraction of the target muscle(s) may mimic the same physiologically relevant responses (e.g., increases in blood flow and velocity) as would occur if the muscle(s) were contracting voluntarily. Cessation of the electrical stimulation during the OFF period may effect relaxation of the muscles, returning the diameter of the venous wall and the venous blood flow and velocity back to pre-stimulation levels (e.g., baseline levels).

Figure 3:
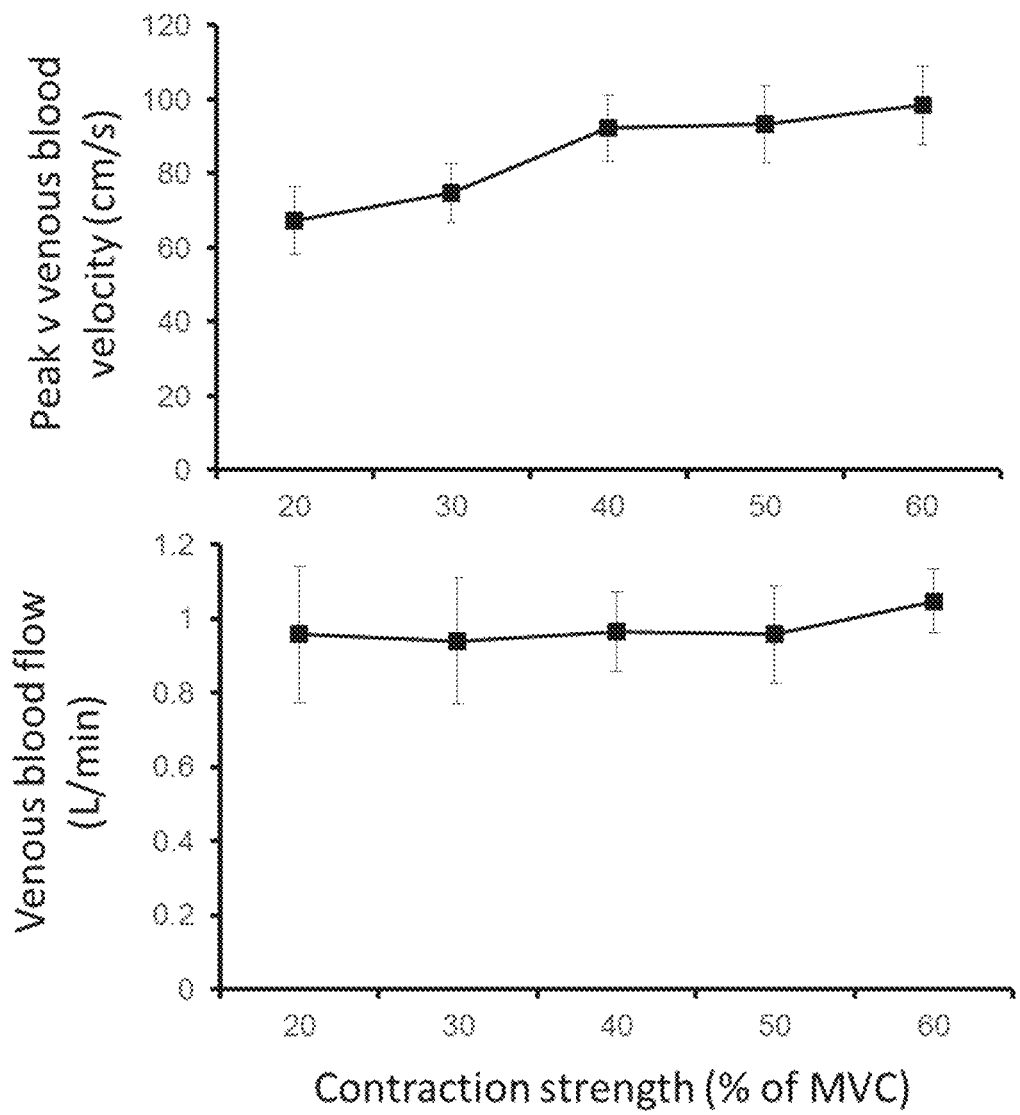
FIG. 3 shows peak venous blood velocity and flow produced by voluntary plantarflexion movements of the ankle at various levels of muscle contraction strengths (mean±standard error of the mean)

Physiological changes in blood flow velocity can be modulated by different levels or strengths of muscle contraction, and can be mimicked by electrically-stimulated muscle contractions. For example, as shown in FIG. 3, peak venous blood velocity and flow produced by voluntary plantarflexion increase when muscle contraction strength increases from 20% to 40% maximal voluntary contraction (MVC), yet further increases were not seen with further increasing strength of contraction. In contrast, blood flow was not affected by the level of muscle contraction strength. Optimally, the parameters of the present apparatus and methodologies may be adapted to mimic such physiological responses. As such, the predetermined period of electrical stimulation (ON) and relaxation (OFF) may be selected to mimic the responses occurring after voluntary 'normal' muscle contractions (e.g., normal physiological muscle pump processes) in individuals that do not suffer from compromised blood flow—that is, individuals who are not at risk of developing venous thromboembolism.

More specifically, notwithstanding that it was observed that venous blood velocity increases in a similar manner in response to muscle contractions lasting 1, 2, 3, 4, and 5 second, the present predetermined 'ON' period may be selected to effect contraction of the target muscle(s) for brief period of time so as to minimize discomfort. In some embodiments, the electrical stimulation and corresponding muscle contraction may be in the range of 0.1 to 5 seconds, in the range of 1-3 seconds, and preferably for approximately 2 seconds. The electrical stimulation and corresponding muscle contraction may be sustained for the entire ON period. The range of electrical stimulation provides a robust range of parameters for evoking physiologically relevant responses, however it would be understood that maintaining muscle contraction and the resulting vessel occlusion for longer periods of time (e.g. beyond 4-5 seconds) may detrimentally increase the risk of thrombus formation and the possibility of muscle fatigue. The train of stimuli may consist of pulse amplitudes suitable to produce a physiological level increase in venous blood velocity and blood flow (e.g., pulse width ranges between 50 and 500 µs, pulse repetition rate ranges from 20 to 60 pulses/sec).

According to embodiments herein, the stimulator 10 may be adapted to electrically stimulate one or more target muscle(s) at a time and in any configuration including, without limitation: 1 channel of stimulation through a pair of electrodes placed over the muscle, 2 channels of stimulation through two pairs of electrodes distributed over the muscle, 3 channels of stimulation through three pairs of electrodes distributed over the muscle, or 4 channels of stimulation through four pairs of electrodes delivered over the muscle. The electrical stimulation may be delivered to either the legs and/or arms of the person, either unilaterally or bilaterally (from one extremity to both upper and lower extremities). Where the electrical stimulation is delivered to multiple target muscles, the stimulation may be delivered alternatingly between muscles (i.e., to one muscle first followed by the next muscle), or simultaneously to all muscles (i.e., producing co-contraction thereof). The electrical stimulation may be delivered to target areas of the legs such as, for example, the muscles below the knee that produce ankle extension (plantarflexion; e.g., gastrocnemius), muscles below the knee that produce ankle flexion (dorsiflexion; e.g., tibialis anterior), muscles above the knew that produce knee flexion (e.g., hamstrings), or muscles above the knee that produce knee extension (e.g., quadriceps).

Following the ON period, the stimulator 10 may be programmed or operable to cease stimulation of the at least one electrode 12, allowing the contracted muscle to "relax" (i.e., not electrically-induced to contract) for the entire OFF period. Cessation of electrical stimulation during the OFF period may last in the range of 0.5 to 10 minutes, and may be in the range of 1 to 5 minutes, and may preferably be approximately 3 minutes. It should be understood that muscle relaxation between bouts of stimulation prevents muscle fatigue, enabling the treatment to be administered for significantly longer periods of time (e.g., ~ up to 24 hours per day or longer). However, longer periods of relaxation (e.g., greater than 3-8 minutes in duration) and the ensuing blood stasis during the relaxation period, may be detrimental by increasing the risk of thrombus formation, eliminating any treatment benefit.

Following the OFF period, the stimulator 10 may be programmed or operable to re-initiate the electrical stimulation, reactivating contraction of the target muscle(s) for a second, subsequent ON period. The second ON period is then followed by a second OFF period, and so on for the entire duration of the present paradigm. For example, in embodiments herein, an optimum cyclic pattern of stimulation to mitigate or prevent DVT may comprise a brief ON period of stimulation for about 1-2 seconds, every 3-5 minutes for a 24 hour treatment period. The present treatment may be used alone or in combination with other prophylactic treatments such as anticoagulants.

According to embodiments herein, a device for intermittently electrically stimulating the at least one target muscle (s) in a person having compromised blood flow for mitigating or preventing venous blood stasis, is provided. The device may comprise at least one electrode 12 adapted to electrically stimulate the at least one target muscle, at least one stimulator 10, electrically coupled to the at least one electrodes 12 and programmed to initiate the at least one electrode 12 to electrically stimulate the at least one target muscle, increasing venous blood flow and venous blood velocity in at least one deep vein associated with, or in the region of, the target muscle, for a predetermined period of stimulation and to cease electrical stimulation for a predetermined period of cessation, returning venous blood flow and blood velocity in the deep veins to pre-stimulation levels.

The present device may be small, light, easy to use, and fully contained (i.e., minimized external connections eliminating the need for pumps). The present device may also be silent, eliminating patient disruption during sleep. The device may also be turned off through a simple switch without the need to remove it (i.e. without having to take it off). For example, in embodiments herein, the present device may be integrated into flexible, comfortable clothing or a garment configured for the application of electrical stimulation, making treatment possible even after the person has left the hospital. For example, the present device may comprise a wrap, a sleeve or sock-type garment. In embodiments herein, the device can be comprised of a small electrical stimulator (e.g., with 1 to 8 channels of stimulation), intelligent software inside the stimulator that produces the intermittent electrical stimulation pattern, and electrodes that are placed in contact with the skin to deliver the electrical stimulus to the muscles. For example, a comfortable garment may be used for holding the electrodes 12 in place and preventing their dislodgement, dislocation, or rolling while the person moves about.

It should be understood that, while IPC systems are mostly available during a hospital stay in acute care, the present apparatus and method can "leave" acute care with the person and be used in tertiary care centres as well as at home. This is advantageous given that DVTs and subsequent PEs are also common after discharge from acute care. For example, for people with total hip or knee replacement, the incidence rate of DVT after discharge from acute care is as high as 75%. Additionally, because the present apparatus and method can produce active contractions of the muscles, they have the unique ability (compared to IPC) to retain muscle health (e.g., muscle mass and contractile strength) in immobilized people, thus reducing the incidence of muscle atrophy and other secondary complications such as spasticity.

It is contemplated that other uses of the present apparatus and method can include prevention of edema formation in people with peripheral vascular disease or heart failure and people with diabetes, elevation of blood pressure in people with orthostatic hypotension or syncope, preservation of range of motion in people with reduced mobility and prevention of contractures in people with neural injuries or diseases such as stroke, spinal cord injury or traumatic brain injury. It is further contemplated that other uses of the present apparatus and method can include use by individuals who are not necessarily hospitalized but may be at risk of DVT for other reasons, including the nature of their work or lifestyle.

EXAMPLE

According to embodiments herein, the present apparatus and methodologies, consisting of a brief predetermined periods of intermittent electrical stimulation followed by predetermined long durations of stimulus cessation, were provided to the calf muscles of users. In the present example, it was observed that an optimal predetermined duration of stimulation may be approximately 2 seconds, with pulse amplitude capable of producing 30% maximal voluntary contraction (i.e. muscle contraction strength), pulse width of 200 µs, pulse frequency of 40 Hz, repeated approximately every three to five minutes (as further defined herein).

Figure 4:
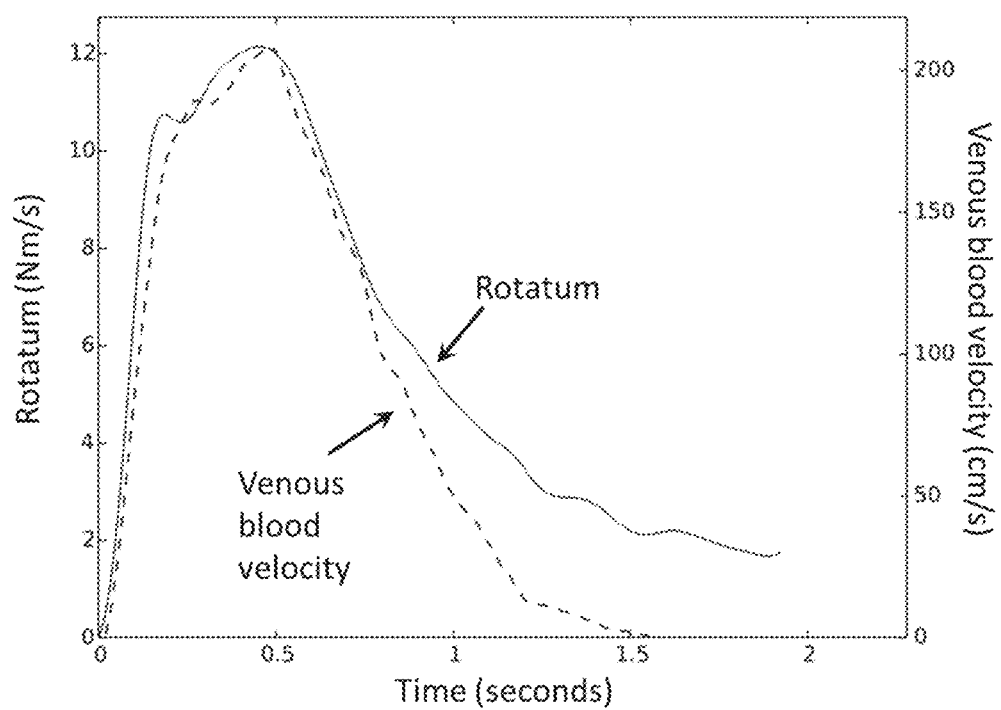
FIG. 4 shows the changes in venous blood velocity due to muscle contraction produced by a 2 second stimulation duration (e.g. "ON" period)

Having regard to FIG. 4, when venous blood flow in the user's popliteal vein was recorded, an increase in venous blood flow was detected that closely follows the rate of increase in muscle torque (rotatum), demonstrating a clear relationship between changes in venous blood velocity and muscle action. Further, when peak venous velocity and fold increase in peak venous blood velocity relative to baseline (as a function of muscle contractions produced by various durations of stimulation phase—1, 2, 3, 4, and 5 secs) were measured, all durations of the stimulation phase produced similar responses (data not shown), that is—there were no significant differences in peak blood velocity or fold increase in peak blood velocity relative to baseline between any durations of the stimulation phase. As such, increases in peak venous blood velocity produced by the present paradigm are observed to be similar to those seen during/following voluntary muscle contractions, demonstrating that the present stimulation paradigm improves peak blood velocity in a manner similar to voluntary muscle contractions. Such an effect is not achieved in known devices using a single pulse or brief train repeated 30-120 times per min to mimic the heart beat (which often produce less than 4 fold increases in venous blood velocity).

Figure 5:
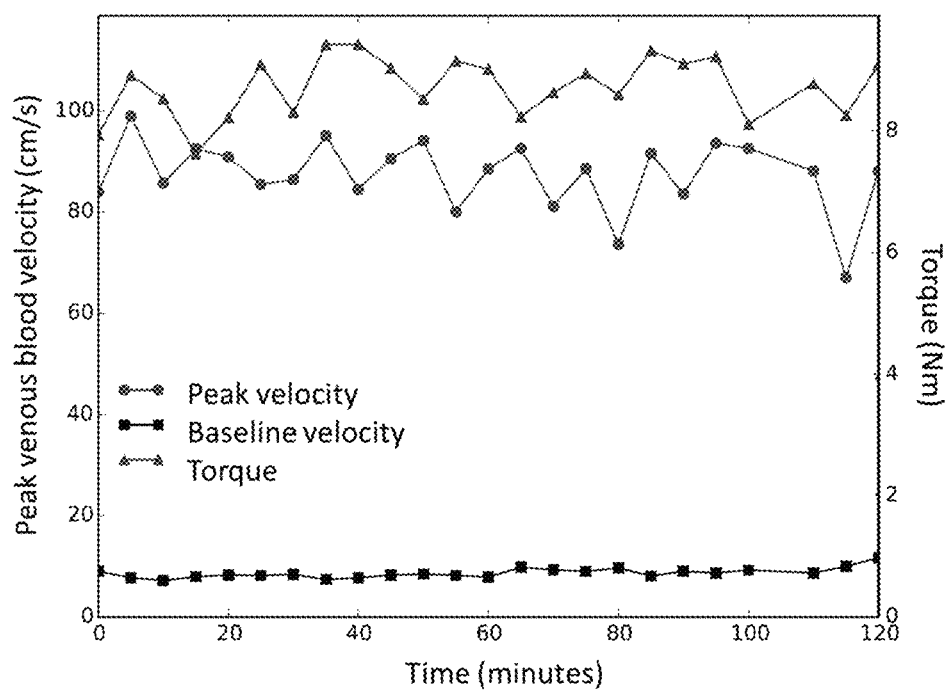
FIG. 5 shows the stability of responses elicited by 2 second stimulation ON periods delivered every 5 minutes for 2 hours in one study participant.
Figure 6:
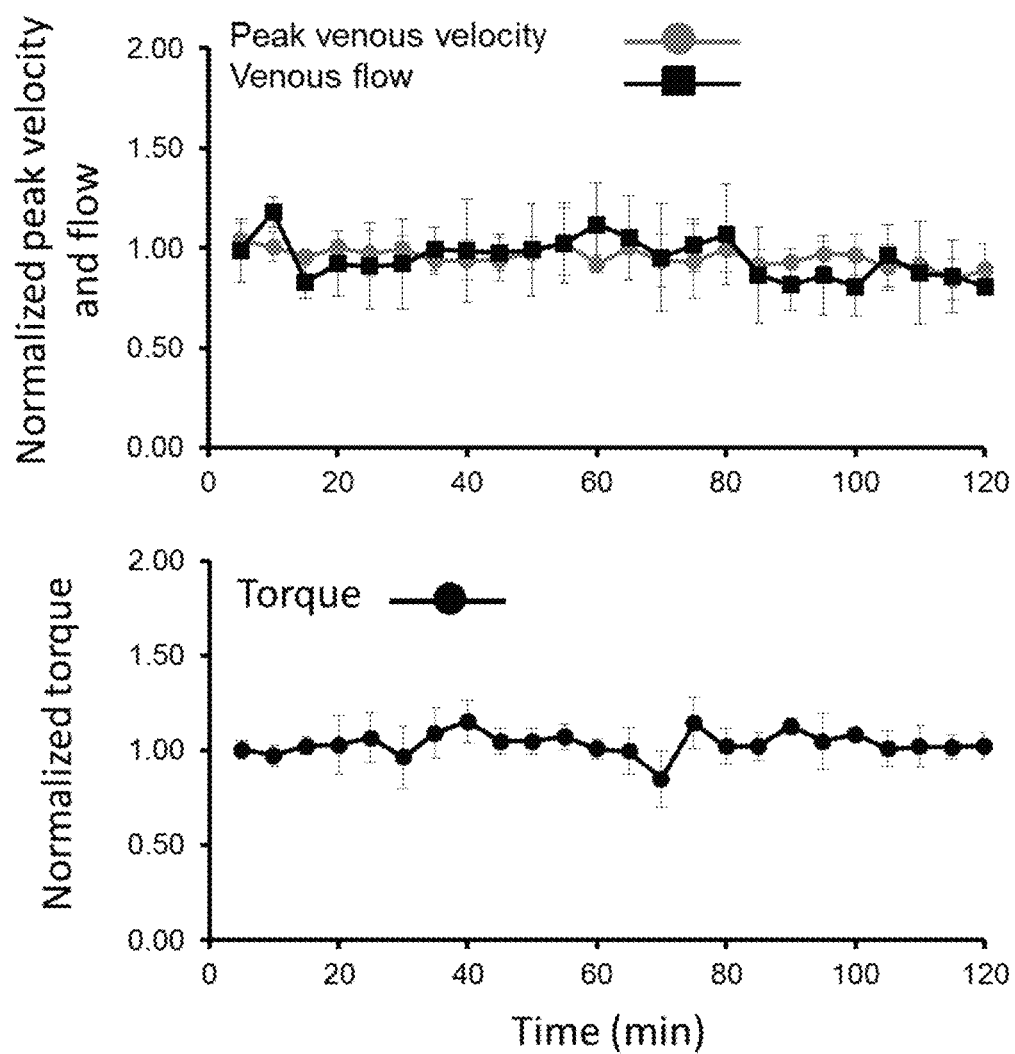
FIG. 6 shows the stability of response elicited by 2 second stimulation ON periods every 5 minutes for 2 hours in a group of participants.

Having regard to FIG. 5, the stability of the level of peak venous blood velocity generated was observed by eliciting contractions with a 2 second stimulation train every 5 minutes over a 2 hour period. Both the torques produced by the repeated contractions and the baseline (pre-stimulation) of peak venous blood velocity remained stable throughout the 2 hour period, demonstrating an absence of muscle fatigue and highlighting an advantage of the present paradigm, its ability to be used for extended durations of time (e.g., up to 24 hours a day). Having regard to FIG. 6, there were no differences in blood velocity, flow or torque over the 2 hour period, further demonstrating an absence of a degradation of physiological responses over long periods of time. The robustness of the present stimulation paradigm allows for increases in venous blood flow and venous blood velocity in deep veins associated with, or in the localized region of the target muscles, and may also cause similar increases in deep veins less localized or not within the proximal region of the target muscles. Such a characteristic not achieved in known systems that only generate small increases relative to baseline (because the pulses are too short or do not form a full muscle contraction).

Figure 7:
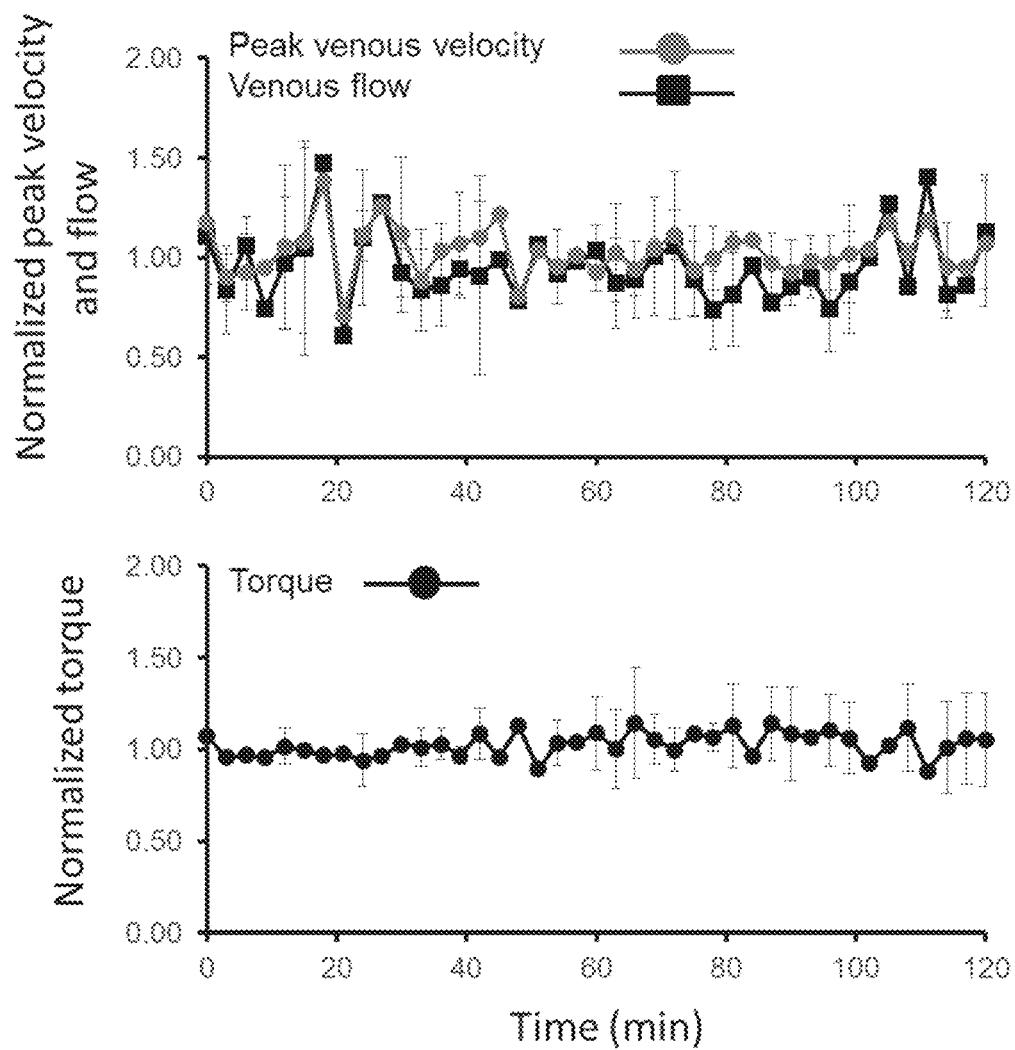
FIG. 7 shows the stability of response elicited by 2 second stimulation ON periods every 3 minutes for 2 hours.

Having regard to FIG. 7, the stability of the level of peak venous blood velocity generated was also observed by eliciting contractions with a 2 second stimulation train every 3 minutes for 2 hours. Both the torques produced by the repeated contractions and the baseline (pre-stimulation) of peak venous blood velocity remained stable throughout the 2 hour period, further demonstrating an absence of muscle fatigue and degradation of physiological responses, enabling the present paradigm to be used to effectively mitigate and prevent DVT by eliciting muscle contractions that increase blood velocity and flow before clots form during periods of blood stasis.

A visual analog scale (VAS), which is a psychometric response scale used to measure the level of discomfort and pain as well as other subject characteristics or attitudes, was used to measure and record the person's pain experience at each stimulation phase (e.g., 1, 2, 3, 4, and 5 secs of stimulation). The scale is continuous between 0 and 10, where 0 refers to no discomfort or pain and 10 refers to maximal discomfort or pain. Across all stimulation phases, the VAS score was <2.5, meaning that none of the people receiving the present methodologies experienced any discomfort or pain during any of the stimulation durations. The present system is very well tolerated even when the longest durations of the stimulation phase is used. Further, the present system may also mitigate other known symptoms associated with reduced mobility, such as muscle spasticity and subsequent contractures.

Broadly stated, the present system provides apparatus and methodologies for mitigating or preventing venous blood stasis and related injuries, such as venous thromboembolism, deep vein thrombosis, pulmonary edema, in individuals with compromised mobility and/or blood flow. It is understood that the pattern of electrical stimulation described herein can be compatible with the timelines for formation of thrombotic factors, and optimally selected to prevent blood stasis without causing muscle fatigue enabling the paradigm to be used for days or weeks at a time. For example, it is believed that thrombotic factors begin to form after 2-7 minutes of stasis. Therefore, the rest period associated with the present pattern of stimulation is also compatible with the physiological processes leading to thrombosis.

Although a few embodiments have been shown and described, it will be appreciated by those skilled in the art that various changes and modifications can be made to these embodiments without changing or departing from their scope, intent or functionality. The terms and expressions used in the preceding specification have been used herein as terms of description and not of limitation, and there is no intention in the use of such terms and expressions of excluding equivalents of the features shown and described or portions thereof.

We claim:

1. A method of electrically stimulating at least one target muscle for mitigating or preventing venous blood stasis in a person having compromised blood flow, the method comprising:
    providing at least one electrode adapted for electrically stimulating the at least one target muscle causing fused tetanic contraction of at least one target muscle and repeating cycles of:
        initiating the at least one electrode to electrically stimulate the at least one target muscle for a predetermined period of stimulation in the range of 1 to 3 seconds, contracting the at least one target muscle and increasing venous blood flow and venous blood velocity in deep veins associated with the at least one target muscle, and
        ceasing the electrical stimulus for a predetermined period of cessation in the range of 1 to 5 minutes, relaxing the at least one target muscle and returning venous blood flow and venous blood velocity in the deep veins to pre-stimulation levels,
        wherein the predetermined period of cessation is longer than the predetermined period of stimulation.

2. The method as defined in claim 1, wherein the method comprises the mitigation or prevention of venous thromboembolism.

3. The method as defined in claim 2, wherein the venous thromboembolism comprises deep vein thrombosis or pulmonary embolism.

4. The method as defined in claim 1, wherein the predetermined periods of electrical stimulation and cessation are selected to mimic mobilization of venous blood flow and venous blood velocity following the fused tetanic muscle contractions of the at least one target muscle.

5. The method as defined in claim 1, wherein the predetermined periods of stimulation and cessation are selected to mimic physiological responses following the fused tetanic muscle contractions in the at least one target muscle.

6. The method as defined in claim 1, wherein the predetermined period of stimulation is approximately 2 seconds.

7. The method as defined in claim 1, wherein the predetermined period of cessation is approximately 3 minutes.

8. The method as defined in claim 1, wherein the predetermined period of stimulation comprises a brief bout of stimulation lasting 2 seconds and repeated every 3 minutes.

9. The method as defined in claim 1, wherein the cycles of predetermined stimulation and cessation are repeated for a period of up to 24 hours per day.

10. The method as defined in claim 1, wherein the predetermined period of stimulation is approximately 1 second.

11. The method as defined in claim 1, wherein the predetermined period of stimulation comprises a brief bout of stimulation lasting 1 second and repeated every 3 minutes.

12. The method as defined in claim 1, wherein stimulation of the at least one target muscle comprises at least two muscles and is alternated between the at least two muscles.

13. A device for electrically stimulating at least one target muscle for mitigating or preventing venous blood stasis in a person having compromised blood flow, the device comprising:
    at least one electrode adapted to electrically stimulate the at least one target muscle causing fused tetanic contraction of the at least one target muscle,
    at least one stimulator, electrically coupled to the at least one electrode and programmed to initiate the at least one electrode to electrically stimulate the at least one target muscle, increasing venous blood flow and venous blood velocity in at least one deep vein associated with the target muscle, for a predetermined period of stimulation in the range of 1 to 3 seconds and to cease electrical stimulation for a predetermined period of cessation in the range of 1 to 5 minutes, returning venous blood flow and venous blood velocity in the deep veins to pre-stimulation levels,
    wherein the predetermined period of cessation is longer than the predetermined period of stimulation.

14. The device as defined in claim 13, wherein the stimulator may be operative to generate a discrete signal, a continuous signal, or a combination thereof.

15. The device as defined in claim 13, wherein the at least one electrode transmits an electrical signal at a frequency in the range of 20 Hz to 60 Hz.

16. The device as defined in claim 13, wherein the at least one electrode transmits an electrical signal at a frequency of approximately 40 Hz.

17. The device as defined in claim 13, wherein the device is provided in a flexible garment.

* * * * *